United States Patent [19]

Hymes et al.

[11] Patent Number: 4,675,009
[45] Date of Patent: Jun. 23, 1987

[54] DRUG DISPENSING DEVICE FOR TRANSDERMAL DELIVERY OF MEDICAMENTS

[75] Inventors: Alan C. Hymes; Lincoln T. Ong, both of Minnetonka; Garry R. Persons, Edina, all of Minn.

[73] Assignee: Lec Tec Corporation, Minnetonka, Minn.

[21] Appl. No.: 845,500

[22] Filed: Mar. 31, 1986

Related U.S. Application Data

[63] Continuation of Ser. No. 561,911, Dec. 15, 1983, abandoned, which is a continuation of Ser. No. 291,611, Aug. 10, 1981, abandoned, and a continuation-in-part of Ser. No. 173,001, Jul. 28, 1980, Pat. No. 4,307,717.

[51] Int. Cl.$^4$ .................. A61F 13/00; A61K 9/70; A61L 15/00; A01N 25/34
[52] U.S. Cl. .................. 604/304; 128/156; 604/897; 604/307; 424/448; 424/449
[58] Field of Search .................. 604/897, 304, 307; 128/156; 424/14, 22, 27, 28

[56] References Cited

U.S. PATENT DOCUMENTS

| | | | |
|---|---|---|---|
| 3,339,546 | 9/1967 | Chen | 604/304 X |
| 4,125,110 | 11/1978 | Hymes | 128/641 |
| 4,274,420 | 6/1981 | Hymes | 128/641 |

Primary Examiner—Nancy Swisher
Attorney, Agent, or Firm—James V. Harmon

[57] ABSTRACT

A flexible, liquid-absorbing, adhesive skin reservoir includes a backing element and a substrate attached to the backing element. The substrate comprises a homogeneous, hydrophilic, stable matrix including a solid phase formed of a synthetic polymer and/or a long chain natural or synthetic polysaccharide, or a combination thereof. The liquid phase of the matrix consists of water, hydric alcohol, carbohydrates and/or proteins in an aqueous solution, and/or a combination thereof. The matrix contains a medicament therein for release to the affected areas for local and/or systemic medicinal effect.

20 Claims, 5 Drawing Figures

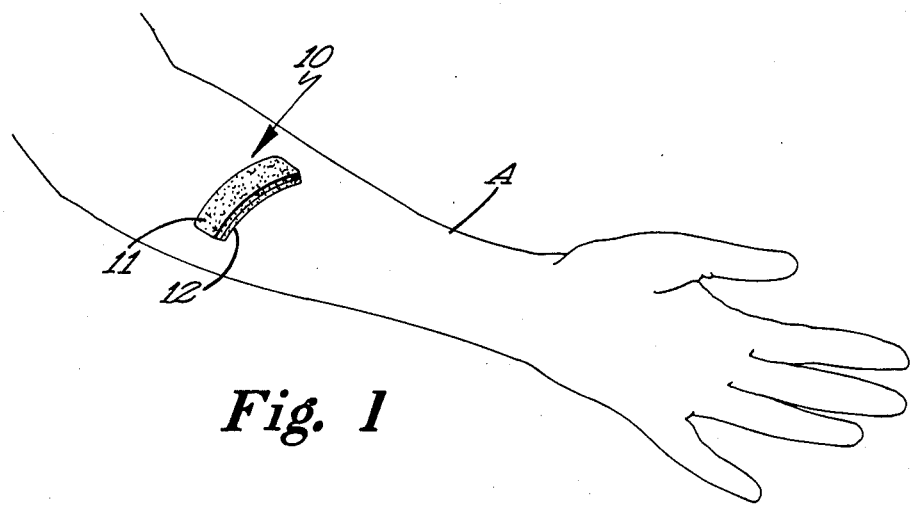
Fig. 1
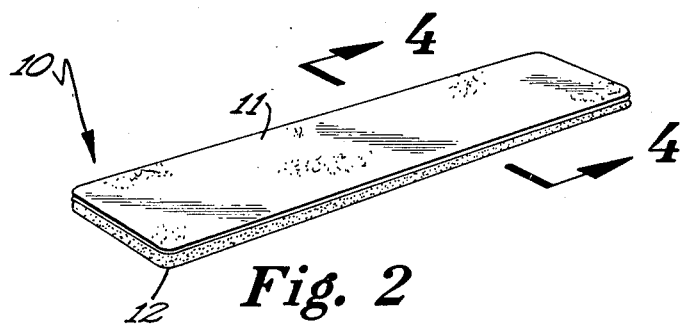
Fig. 2
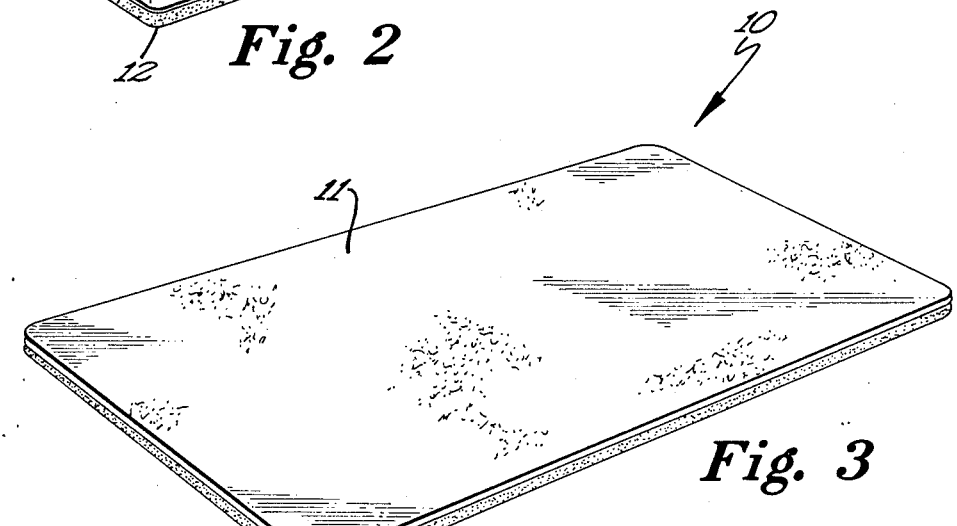
Fig. 3
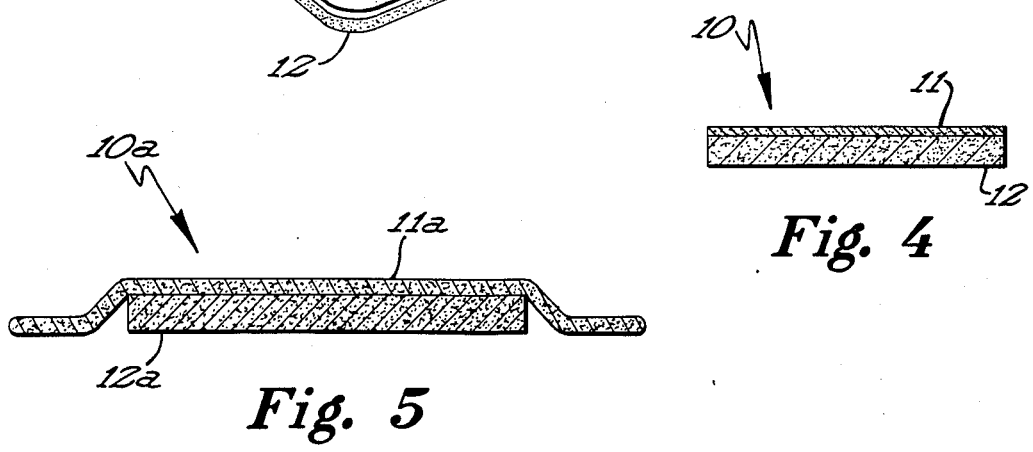
Fig. 4
Fig. 5

DRUG DISPENSING DEVICE FOR TRANSDERMAL DELIVERY OF MEDICAMENTS

This is a continuation of application Ser. No. 561,911 filed Dec. 15, 1983 which was abandoned upon the filing hereof, itself a continuation of Ser. No. 291,611 filed Aug. 10, 1981, now abandoned, and a continuation-in-part of Ser. No. 173,001 filed July 28, 1980, now U.S. Pat. No. 4,307,717

BACKGROUND OF THE INVENTION

This invention relates to an improved skin reservoir which contains a medicament that is topically released into the skin.

Attempts have been made to develop reservoir delivery systems which are self-adhesive and water absorbent. For example, U.S. Pat. No. 3,339,546 discloses a self-adhesive reservoir which is adapted to adhere to moist surfaces such as the moist mucosa of the oral cavity. However, one of the essential materials of this self-adhesive reservoir is an adhesive gum, preferably polyisobutylene, which is hydrophobic. Similarly, U.S. Pat. Nos. 3,598,122 and 3,598,123 disclose reservoirs which contain drugs that are continually released from an adhesive layer. These reservoirs are formed of layered materials which have drugs encapsulated in the adhesive layer. Even though the reservoirs disclosed in these prior art patents are said to be self-adhesive and are satisfactory vehicles for drugs, specific process steps are required for encapsulating or stratifying the drugs.

Hydrophilic polymers plasticized with hydric alcohol and/or water have been used for ostomy gaskets (U.S. Pat. No. 3,640,741) and for the conduction of electrical current to and from the skin (U.S. Pat. Nos. 4,125,110, 4,273,135 and 4,066,078). The polymeric formulations specifically contain organic or inorganic ions physically dissolved in the plasticizers for electron transfer. More recently, Silastic polymers (U.S. Pat. No. 4,336,243) have been used to release a nitroglycerine medicament solubilized in the plasticizer for transfer into a body through the skin. However, this matrix reservoir system tends to dry out and is not self-adherent.

SUMMARY OF THE INVENTION

Therefore, it is a general object of this invention to provide a self-adhesive, novel matrix reservoir in which a medicament is molecularly dispensed for release to the affected area. The matrix reservoir is comprised of a flexible backing element and a self-adhesive substrate which becomes increasingly tacky in the presence of moisture and which absorbs liquid and releases the medicament to the affected area while remaining dimensionally stable.

Another form of the substrate contains cross-linked polysaccharides plasticized with water and/or hydric alcohol which are not self-adhering, but dry very slowly and are dimensionally stable even when in the environment of 100% water.

It is pointed out that the present reservoir system is not formed of a gelatinous base, but is formed of a polymeric base, and is therefore not biodegradable in the manner of certain prior art devices. It is also pointed out that the medicament is progressively released from the reservoir until the contents thereof are substantially diminished so that the reservoir system, in effect, is dynamically altered as a drug dispensing device. When a medicament is incorporated into the reservoir structure, the formation and structure of the basic matrix system is changed because the new molecule may become integrated into the polymeric formation and change the method of formulation. Each medicament is associated with a particular polymer or polymers. These formulations are designed so that the medicament will be available for active and/or passive diffusion into the skin. The skin becomes part of the reservoir system and the matrix reservoir becomes active when applied to the skin.

Finally, and most importantly, the present reservoir system is formed of a hydrophilic substance which moisturizes the skin and enhances absorption of a medicament by building a hydrophilic bridge so that the medicament can diffuse from the reservoir into the skin.

These and other objects and advantages of this invention will more fully appear from the following description made in connection with the accompanying drawings, wherein like reference characters refer to the same or similar parts throughout the several views.

FIGURES OF THE DRAWING

FIG. 1 is a perspective view illustrating the novel reservoir applied to the arm of a patient;

FIG. 2 is a perspective view of a reservoir illustrated in FIG. 1;

FIG. 3 is a perspective view of a large size reservoir;

FIG. 4 is a cross-sectional view taken approximately along line 4—4 of FIG. 2 and looking in the direction of the arrows; and FIG. 5 is a modified form of the reservoir.

DESCRIPTION OF THE PREFERRED EMBODIMENT

The reservoir of the present invention may have adhesive properties for maintaining contact with the skin, as well as possessing a certain amount of elasticity for movement with the skin. The reservoir is intended to be easily handled and is non-irritating to the patient's skin.

Referring now to the drawings, it will be seen that the drug delivery system of the present invention is thereshown. This reservoir, designated generally by the reference numeral 10, includes a backing member 11 and a self-adhesive substrate 12 which is secured to one end surface of the backing. The backing element 11 and the substrate 12 are both illustrated as rectangular sheets of material of uniform thickness. It is pointed out that the reservoir 10 is intended to be regular in shape, but may have any other configuration, although the rectangular shape is preferred. In use, the reservoir is applied with the substrate 12 in direct contact with the skin.

Referring now to FIG. 5, it will be seen that a different embodiment of the reservoir, designated generally by the reference numeral 10a, is thereshown. The reservoir includes a pressure-sensitive adhesive element 11a which serves as the backing element and also serves as the means for securing the bandage to the surface of the skin. The pressure-sensitive adhesive element 11a may be formed of any of the materials used in commercially available adhesive elements, such as a foam-type adhesive element. It will be appreciated that most of the commercially available adhesive elements maintain an excellent bond with the skin.

Primary to the unique structure of the reservoir is the hydrophilic adhesive properties of the substrate which enhance the adhesion thereof to the skin. The substrate not only absorbs moisture, but the substrate becomes tackier as it absorbs moisture.

Alternatively to the hydrophilic adhesive properties, is a very wet, slowly drying and dimensionally stable reservoir made from cross-linked guar in water.

The substrate 12 may be formed from naturally occurring materials such as gum karaya, gum acacia, locust bean gum and other polysaccharides, and synthetically formulated polysaccharides such as guar and celluloses such as carboxy-methyl cellulose. The substrate may also be formed from synthetic polymers such as polyacrylamide and its cogeners, polyacrylic acid molecular weights 250,000, 450,000, 1,000,000 and 4,000,000, and polyacrylamide sold under such trademarks as Reten by Hercules Company. When monomers such as acrylic acid or acrylamide are polymerized, it is necessary to use activators. Activators, which are used during polymerization, may include ferrous sulfate, sodium metabisulfite, potassium persulfate, as set forth in the co-pending application, Ser. No. 424,342. The disclosure of the co-pending application Ser. No. 424,342 is incorporated herein by reference. Alternatively, the polymeric portion may be synthetically made of combined polymers of acrylamide and saccharides (guar) and starch-g-poly made by Henkel Corporation, St. Paul, Minnesota.

The synthetic polymers and/or synthetic or natural gums and other polysaccharides constitute the solid phase of the matrix. The liquid phase of the matrix preferably consists of hydric alcohols such as glycerol and/or propylene glycol, and/or water. Solutions or emulsions of saccharides and/or polysaccharides and/or proteins may also be used in plasticizing the matrix. Alternatively, a combination of a solution or emulsion of polysaccharides, saccharides or proteins may be used in the liquid phase of the matrix.

The substrate 12, which is a stable matrix, includes a solid phase comprising a synthetic polymer mixture, a large molecular weight polysaccharide matrix, or a matrix of a large molecular weight polysaccharide and synthetic polymer. The solids of the matrix comprise 2% to 50% by weight of the matrix. The liquid phase of the matrix, such as hydric alcohol and/or water, comprises 50% to 98% by weight of the matrix. The reservoir also includes a suitable backing member which may include cotton fabric, woven or standard paper, synthetic fabrics, and/or plastics.

The substrate 12 also contains a medicinal substance for release to the surface to which the reservoir is applied. The medicinal substance is molecularly dissolved and/or suspended in the matrix rather than being encapsulated as in the prior art. The medicinal substance may include an antibacterial, antiseptic, or antifunginal agent such as boric acid, bacitracin, acriflavin, formaldehyde, gential violet, mercuric sulfide, mercurochrome, neomycin, and iodine. Nitroglycerine may be used as a coronary vasodilater agent. Suitable antipruretic agents include benzoin, calamine, camphor, menthol, phenol, and sulfer. The substrate may also include frangrances such as cinnamon oil, fir needle oil, lemon oil, peppermint oil, and spearmint. Suitable healing agents include allantoin, Peruvian balsam, Vitamin A, and Vitamin E. Hormonal agents may include hydrocortisone or similar steroids, estrogen, progesterone, and testosterone. Protective agents may include benzoin, charcoal, talc, and zinc oxide. Salicylic acid is a suitable keratolytic agent and methyl salicylate is a suitable rubefacient. An examplary antihistamine is chlorpheniramine. Glucose lowering agents such as insulin and tolbutamide may be used.

It has been found that vinyl acetate dioctyl maleate copolymer may also be advantageously used in forming the solid phase of the matrix. Vinyl acetate dioctyl maleate copolymer (sold under the trademark "Flexbond 150" by Air Products and Chemicals, Inc., and sold under the trademark "Bostik 8761" by the Bostik Company, Inc.) will intensify the tackiness of the reservoir.

Another important gum material which may be used in forming the matrix is a starch graft copolymer sold under the trade name "SGP 502S Absorbent Polymer" by the Henkel Corporation, St. Paul, Minnesota. The starch graft copolymer product is derived from corn starch and acrylonitrile, and is a graft terpolymer of starch, acrylamide and sodium acrylate. The technical name for this starch graft copolymer product is starch-g-poly (acrylamide-co-sodium acrylate). The starch-g-poly material may be used alone to form the substrate or it may be used in combination with a synthetic gum such as acrylamide or a natural gum such as karaya. The starch-g-poly material is very effective as the skin contacting substrate, since it does maintain its structural integrity and is non-toxic.

One of the distinct advantages of the present reservoir system is that it is a hydrophilic substance which prepares the skin for absorbing medicaments. The present reservoir system is not a drug delivery device for merely releasing a drug locally, but also may deliver medicaments transdermally for systemic use.

|  | Nominal Amounts of Ingredients | Range of Ingredients |
| --- | --- | --- |
| EXAMPLE 1 | | |
| Polyacrylamide | 5% | 1–50% |
| Karaya | 38% | 5–45% |
| Glycerol | 55% | 30–70% |
| Povidone-Iodine | 2% | 0.1–10% |
| EXAMPLE 2 | | |
| Polyacrylic acid | 10% | 2–40% |
| Polyacrylamide | 10% | 2–40% |
| Karaya | 18% | 5–45% |
| Glycerol | 60% | 30–70% |
| Povidone-Iodine | 2% | 0.1–10% |
| EXAMPLE 3 | | |
| Polyacrylamide | 15% | 2–40% |
| Polyacrylic acid | 15% | 2–40% |
| Glycerol | 68% | 30–70% |
| Povidone-Iodine | 2% | 0.1–10% |
| EXAMPLE 4 | | |
| Polyacrylamide | 30% | 2–40% |
| Glycerol | 62% | 50–70% |
| Methyl Salicylate | 8% | 0.1–15% |
| EXAMPLE 5 | | |
| Polyacrylamide | 21.5% | 2–40% |
| Polyacrylic acid | 12.5% | 2–40% |
| Glycerol | 42% | 30–70% |
| Vinyl acetate-dioctyl maleate | 16% | 10–20% |
| Methyl salicylate | 8% | 0.1–15% |
| EXAMPLE 6 | | |
| Polyacrylamide | 31% | 2–40% |
| Glycerol | 55% | 30–70% |
| Water | 6% | 1–10% |
| Methyl salicylate | 8% | 0.1–15% |
| EXAMPLE 7 | | |
| Povidone-Iodine | 2% | 0.1–10% |
| Hydroxy-propylcellulose (Klucel) | 6% | 0.1–10% |
| Glycerin | 56% | 30–70% |
| Water | 6% | 0.1–10% |
| Polyacrylamide (Reten 421) | 30% | 2–40% |
| EXAMPLE 8 | | |

-continued

| | Nominal Amounts of Ingredients | Range of Ingredients |
|---|---|---|
| Povidone-Iodine | 10% | 0.1–15% |
| Reten 421 (polyacrylamide) | 5% | 2–40% |
| Karaya | 35% | 5–45% |
| Glycerol | 50% | 30–70% |
| EXAMPLE 9 | | |
| Povidone-Iodine | 2% | 0.1–10% |
| Karaya | 43% | 5–45% |
| Glycerol | 55% | 30–70% |
| EXAMPLE 10 | | |
| Camphor | 2% | 0.1–5% |
| Methylene bisacrylamide | 3% | 0.1–10% |
| Acrylic acid | 8% | 0.1–10% |
| Glycerol | 86% | 45–90% |
| Activators* | 1% | 0.1–2% |
| *Potassium persulfate 0.6% | | |
| Sodium metabisulfate 0.2% | | |
| Ferrous sulfate 0.1% | | |
| EXAMPLE 11 | | |
| Camphor | 2% | 0.1–5% |
| Glycerol | 55% | 30–70% |
| Karaya | 43% | 5–45% |
| EXAMPLE 12 | | |
| Methyl salicylate | 2% | 0.1–10% |
| Methylene bisacrylamide | 5% | 0.1–10% |
| Acrylic acid | 8% | 0.1–10% |
| Glycerol | 84% | 30–70% |
| Activators | 1% | 0.1–2% |
| EXAMPLE 13 | | |
| Methyl salicylate | 8% | 0.1–15% |
| Acrylic acid | 2% | 0.1–10% |
| Methylene bisacrylamide | 1% | 0.1–10% |
| Glycerol | 48% | 30–70% |
| Karaya | 40% | 5–45% |
| Activators | 1% | 0.1–2% |
| EXAMPLE 14 | | |
| Starch-g-poly | 35% | 15–50% |
| Glycerol | 35% | 30–70% |
| 10% Nitroglycerine in propylene glycol | 30% | 10–40% |
| EXAMPLE 15 | | |
| Starch-g-poly | 25% | 1–40% |
| Glycerol | 30% | 30–70% |
| Karaya | 15% | 5–30% |
| 10% Nitroglycerine in propylene glycol | 30% | 10–40% |
| EXAMPLE 16 | | |
| Guar derivative | 1.9% | 1–3% |
| Potassium pyroantimonate crosslinkers | 0.1% | 0.03–1.0% |
| Water | 88% | 80–95% |
| 50% Isosorbide dinitrate in lactose | 10% | 5–20% |
| EXAMPLE 17 | | |
| Guar derivative | 3.4% | 0.8–7% |
| Potassium pyroantimonate crosslinker | 0.6% | 0.1–1% |
| Karaya | 15% | 5–25% |
| Glycerol | 35% | 25–45% |
| 50% Isosorbide dinitrate in lactose | 10% | 5–20% |
| Water | 36% | 25–55% |
| EXAMPLE 18 | | |
| Ester of (α-, β-olefinically | 49.08% | 10–90% |
| Unsaturated carboxylic acid crosslinker | 0.02% | 0.01–0.05% |
| Glycerol | 20% | 15–50% |
| 10% Nitroglycerine in propylene glycol | 30% | 15–50% |
| EXAMPLE 19 | | |
| Locust bean gum | 2.5% | 0.25–5% |
| Xyanthan gum | 2.5% | 0.25–5% |
| Water | 85% | 75–95% |
| 50% Isosorbide dinitrate in lactose | 10% | 4.5–20% |
| EXAMPLE 20 | | |
| Karaya | 30% | 20–50% |
| Glycerol | 55% | 30–70% |
| Salicylic acid | 15% | 8–20% |
| EXAMPLE 21 | | |
| Karaya | 35% | 25–45% |
| Glycerol | 45% | 35–70% |
| Aloe Vera | 20% | 5–30% |

It is pointed out that 50% glucose in water can be substituted in the above examples for glycerol in equivalent percentages. Similarly, 5–10% albumen in water or 5–10% casein in water can be substituted in equivalent percentages for glycerol or hydric alcohols in the above example. Combinations of aqueous solutions of carbohydrates or larger molecular weight polysaccharides and/or aqueous solutions of proteins may also be substituted for glycerol or other hydric alcohols.

What is claimed is:

1. A flexible, liquid-absorbent, nonbiodegradable adhesive reservoir to be applied to a patient comprising: a flexible backing element selected from the group consisting of cotton, paper, synthetic fabric and plastic, a substrate attached to said backing element comprising a homogeneous, hydrophilic, stable matrix being sufficiently pliant to conform to the shape of the body contours, said matrix including a solid face comprising about 1% to 50% of the total weight of the matrix and formed for a high-molecular natural and/or synthetic polysaccharide and/or a synthetic polymer selected from the group consisting of: polyacrylic acid, polyacrylamide and their cogeners, vinyl acetate ethylene copolymer, vinyl acetate dioctyl maleate copolymer, synthetic and natural polysacchacrid gums, starch-g-poly, and a crosslinked ester of α, β, olefinically unsaturated carboxylic acid and a liquid phase hydrating the matrix and converting the matrix to a hydrocolloidal suspension, said liquid phase consisting of polyhydric alcohol solutions or dispersions selected from the group consisting of water solutions of carbohydrate, and/or protein, and/or polyhydric alcohol, and comprising from 50% to 98% by weight of the matrix, said matrix containing a medicament selected from the group consisting of cardiovascular drugs, vasodialators, anti-arrythmic drugs and anti-hypertensive drugs, and antibacterial agent, antiseptic agent, anti-inflammatory agent, anti-pruretic agent, hormonal agent, keratolytic agent, skin protective agent and a rubefacient agent, said reservoir when applied to a patient forming a hydrophilic bridge with the patient's skin to allow the progressive release of the medicament across the hydrophilic bridge the hydrophilic hydrated matrix maintaining the medicament in a hydrated state allowing for free diffusion and dynamic tranfer thereof through the reservoir to the skin interface and the hydrated state of the matrix providing hydrophilic adhesive properties rendering the substrate tacky to enhance adhesion to the skin.

2. The reservoir as defined in claim 1 wherein said liquid phase comprises a water solution of a polysaccharide.

3. The reservoir as defined in claim 1 wherein said liquid phase comprises a polyhydric alcohol.

4. The reservoir as defined in claim 1 wherein said liquid phase comprises a water solution of a protein.

5. The reservoir as defined in claim 1 wherein the solid phase of said matrix includes a natural gum selected from the group consisting of gum karaya, gum acacia, and locust bean gum.

6. The reservoir as defined in claim 5 wherein said matrix is comprised of 5% to 45% by weight of gum karaya, 2% to 40% by weight of polyacrylamide, and 30% to 70% by weight of glycerol.

7. The reservoir as defined in claim 1 wherein said matrix is comprised of 10% to 50% by weight of polyacrylamide and 30% to 70% by weight of glycerol.

8. The reservoir as defined in claim 1 wherein said matrix is formed of 2% to 40% by weight of polyacrylamide, 2% to 40% by weight of polyacrylic acid, and 30% to 70% by weight of glycerol.

9. The reservoir as defined in claim 1 wherein said matrix is formed of 2% to 50% by weight of polyacrylic acid and 30% to 70% by weight of glycerol.

10. The reservoir as defined in claim 1 wherein said matrix is formed of 15% to 50% by weight of starch-g-poly, 30% to 70% by weight of glycerol, and 10% to 40% by weight of 10% nitroglycerine in propylene glycerol.

11. The reservoir as defined in claim 1 wherein said matrix is formed of 1% to 3% by weight of guar derivative, 0.03% to 1% by weight of potassium pyroantimonate crosslinkers, 80% to 95% by weight of water and 5% to 20% by weight of 50% isosorbide dinitrate in lactose.

12. The reservoir as defined in claim 1 wherein said matrix is formed of 0.8% to 7% by weight of guar derivative, 0.1% to 1% by weight of potassium pyroantimonate crosslinkers, 5% to 25% by weight of karaya, 25% to 45% by weight of glycerol, and 5% to 20% by weight of 50% isosorbide dinitrate.

13. The reservoir as defined in claim 1 wherein said matrix is formed of 0.25% to 5% by weight of locust bean gum, 0.25% to 5% by weight of xyanthan gum, 75% to 95% by weight of water, and 4.5% to 20% by weight of 50% isosorbide dinitrate in lactose.

14. The reservoir as defined in claim 1 wherein said matrix is formed of 10% to 90% by weight of ester of a,B,olefinically unsaturated carboxylic acid, 0.01% to 0.05% by weight of potassium pyroantimonate crosslinkers, 15% to 50% by weight of glycerol, and 15% to 50% by weight of 10% nitroglycerine in propolyene glycol.

15. The reservoir as defined in claim 3 wherein said medicament comprises 0.1% to 15% by weight of povidone-iodine.

16. The reservoir as defined in claim 3 wherein said medicament comprises 0.1% to 5% by weight of camphor.

17. The reservoir as defined in claim 5 wherein said medicament comprises 0.1% to 5% by weight of camphor.

18. The reservoir as defined in claim 3 wherein said medicament comprises 0.1% to 15% by weight of methyl salicylate.

19. The reservoir as defined in claim 1 wherein said matrix has adhesive properties whereby the surface which contacts the skin defines said adhesive surface.

20. The reservoir as defined in claim 1 wherein said backing element is a pressure sensitive adhesive element and defines said adhesive surface which contacts the patient's skin.

* * * * *

UNITED STATES PATENT AND TRADEMARK OFFICE
CERTIFICATE OF CORRECTION

PATENT NO. : 4,675,009
DATED : June 23, 1987
INVENTOR(S) : Alan C. Hymes et al

It is certified that error appears in the above-identified patent and that said Letters Patent is hereby corrected as shown below:

Column 6, line 20, "face" should read -- phase --

Column 6, line 49, "tranfer" should read -- transfer --

Column 7, line 30 "xyanthan" should read -- xanthan --.

Column 8, line 5, "aB" should read --$X\beta$ --

Signed and Sealed this

Second Day of February, 1988

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,675,009
DATED : June 23, 1987
INVENTOR(S) : Alan C. Hymes et al.

It is certified that error appears in the above-identified patent and that said Letters Patent is hereby corrected as shown below:

Column 6, line 20, "face" should read -- phase --.

Column 6, line 49, "tranfer" should read -- transfer --.

Column 7, line 30, "xyanthan" should read -- xanthan --.

Column 8, line 5, "aB" should read -- $\alpha\beta$ --.

This certificate supersedes Certificate of Correction issued February 2, 1988.

Signed and Sealed this

Second Day of August, 1988

Attest:

DONALD J. QUIGG

Attesting Officer   Commissioner of Patents and Trademarks